United States Patent
Regnier et al.

(10) Patent No.: US 12,255,556 B2
(45) Date of Patent: Mar. 18, 2025

(54) PIEZOELECTRIC-TRANSDUCER ENERGY HARVESTER, IN PARTICULAR FOR POWERING AN AUTONOMOUS CARDIAC CAPSULE, WITH A BENDING STIFFNESS GRADIENT OSCILLATING STRUCTURE

(71) Applicant: CAIRDAC, Antony (FR)

(72) Inventors: Willy Regnier, Longjumeau (FR); An Nguyen-Dinh, La Riche (FR)

(73) Assignee: CAIRDAC, Antony (FR)

( * ) Notice: Subject to any disclaimer, the term of this patent is extended or adjusted under 35 U.S.C. 154(b) by 20 days.

(21) Appl. No.: 18/508,399

(22) Filed: Nov. 14, 2023

(65) Prior Publication Data
US 2024/0313671 A1    Sep. 19, 2024

(30) Foreign Application Priority Data
Mar. 17, 2023   (EP) .................................... 23315053

(51) Int. Cl.
*H02N 2/18* (2006.01)
*A61N 1/372* (2006.01)
*H02N 2/00* (2006.01)

(52) U.S. Cl.
CPC ......... *H02N 2/186* (2013.01); *A61N 1/37205* (2013.01); *H02N 2/006* (2013.01);
(Continued)

(58) Field of Classification Search
CPC .... H10N 30/30; H10N 30/302; H10N 30/304; H10N 30/306; H10N 30/308; H02N 2/18;
(Continued)

(56) References Cited

U.S. PATENT DOCUMENTS

| | | | |
|---|---|---|---|
| 2007/0114890 A1* | 5/2007 | Churchill | H10N 30/306 310/339 |
| 2011/0156532 A1* | 6/2011 | Churchill | G01L 1/26 310/319 |
| 2015/0008792 A1 | 1/2015 | Gong et al. | |

FOREIGN PATENT DOCUMENTS

| | | |
|---|---|---|
| EP | 3 319 133 A1 | 5/2018 |
| EP | 3 876 386 A1 | 9/2021 |
| WO | 2017/195014 A1 | 11/2017 |

OTHER PUBLICATIONS

European Patent Office, Search Report issued in corresponding Application No. EP 23315053, mailed Sep. 5, 2023.

* cited by examiner

*Primary Examiner* — Derek J Rosenau
(74) *Attorney, Agent, or Firm* — Stites & Harbison, PLLC; Jeffrey A. Haeberlin

(57) ABSTRACT

The harvester comprises a pendular unit comprising a beam that is elastically deformable in bending, a mount clamping a proximal end of the beam, and an inertial mass mounted at a free, distal end of the beam. The beam converts into an oscillating electric signal a mechanical energy produced by pendular unit oscillations. The beam comprises a flexible structure including a central core, a piezoelectric layer on at least one face of the central core, and at least one surface electrode on an external face of the piezoelectric layer. The central core of the flexible structure is made of a semiconductor material adapted to form an integrated circuit substrate. The substrate made of a semiconductor material of the central core includes monolithic integrated structures, and the arrangement, over the extend of the central core substrate, of said integrated structures forms in the longitudinal direction a plurality of successive areas having different bending stiffness coefficients from an area to another.

14 Claims, 7 Drawing Sheets

(52) U.S. Cl.
CPC ........... *H02N 2/0085* (2013.01); *H02N 2/181* (2013.01); *H02N 2/22* (2013.01)

(58) Field of Classification Search
CPC ........ H02N 2/181; H02N 2/183; H02N 2/185; H02N 2/186; H02N 2/188
USPC ........................................................ 310/339
See application file for complete search history.

PIEZOELECTRIC-TRANSDUCER ENERGY HARVESTER, IN PARTICULAR FOR POWERING AN AUTONOMOUS CARDIAC CAPSULE, WITH A BENDING STIFFNESS GRADIENT OSCILLATING STRUCTURE

BACKGROUND OF THE INVENTION

Technical Field

The invention relates to energy harvesting devices, also called "harvesters" or "scavengers", which collect the mechanical energy resulting from various movements they undergo and convert this mechanical energy into electrical energy.

It more particularly relates to the harvesting devices of the so-called "PEH" (Piezoelectric Energy Harvester) type, which use as a mechanical-electrical transducer an oscillating piezoelectric beam coupled to an inertial mobile mass.

The invention will be more particularly described in an application of such energy harvesters to autonomous medical devices, in particular devices of the autonomous implantable capsule type, in particular those which are intended to be implanted in a heart cavity.

This application, although being particularly advantageous, must however not be considered as limiting the invention, whose teachings can be applied to many other types of autonomous devices incorporating an energy harvester of the PEH type, whether these devices are implantable or not, medical or not.

State of the Art

In the field of medical implants, recent advances in miniaturization of active devices and the advances in life sciences allow from now on the development of a wide variety of fully autonomous, miniaturized implantable systems, for monitoring, diagnosis or treatment purposes. Such devices implement less invasive implantation procedures, provide more comfort, increased performances, and often open up access to new types of diagnoses and treatments.

When applied to the field of medical implants, the invention more particularly relates to those devices which incorporate a self-powering system comprising a mechanical energy harvester associated with an integrated energy storage element, such as a rechargeable battery or a high-performance capacitor.

Indeed, one of the critical aspects of these miniaturized devices is power autonomy. The life duration of such an implant being about 8-10 years, given the very small dimensions it is not possible to use a conventional battery, even a high-density one.

The energy harvesting device addresses this drawback by collecting the mechanical energy resulting from the various movements undergone by the body of the implanted device. Those movements may have for origin a certain number of phenomena occurring for example at the rhythm of the heartbeats, such as periodic shakes of the wall on which the implant is anchored, heart tissue vibrations linked i.a. to closings and openings of the heart valves, or also blood flow rate variations in the surrounding environment, which stress the implant and make it oscillate at the rhythm of the flow rate variations.

The mechanical energy collected by the harvester is converted into electrical energy (voltage or current), by means of a suitable mechanical-electrical transducer, for powering the various circuits and sensors of the device and charging the energy storage element. This power supply system allows the device to operate in full power autonomy for its whole lifetime.

This energy harvesting technique is particularly well adapted for powering the implanted autonomous capsules having no physical connection with a remote device. Such capsules are called for this reason "leadless capsules", for distinguishing them from the electrodes or sensors arranged at the distal end of a lead, through the whole length of which run one or several conductors connected to a generator itself connected to the opposite, proximal end.

The invention is nevertheless not limited to a particular type of capsule, nor even of leadless implant, and is applicable as well to many other types of implantable medical devices, whatever the operational purpose thereof, cardiac or other, medical or not.

In the cardiac application case, the leadless capsule continuously monitors the patient's rhythm and if necessary issues to the heart electrical pulses for pacing, resynchronization and/or defibrillation in case of rhythm disorders detected by the capsule. The capsule further comprises various electronic circuits, sensors, etc., as well as wireless communication transmission/reception means for the remote exchange of data, the whole being integrated in a body of very small size able to be implanted at sites of difficult access or leaving little available space, such as the ventricle apex, the inner wall of the atrium, etc.

WO 2019/001829 A1 (Cairdac) describes an example of such a leadless intracardial capsule.

The invention more particularly relates to capsules or similar implantable devices whose energy harvester is of the PEH type, i.e. using a piezoelectric transducer and an inertial pendular unit subjected to the external stresses described hereinabove. The inertial pendular unit comprises, within the capsule body, a mobile mass called "seismic mass" or "inertial mass", which is driven according to the movements of the capsule, permanently subjected to the various external stresses described hereinabove. After each of these stresses, the inertial mass, which is coupled to an elastically deformable element, can either oscillate at its natural frequency (if the latter is designed to be close to the frequency of the stresses) with progressive damping in accordance with the damping mode (narrow band), or be deformed under the effect of acceleration in forced mode (wide band).

The mechanical energy of the oscillation is converted into electrical energy by a mechanical-electrical transducer producing an electrical signal. This mechanical-electrical transducer may be in particular a piezoelectric transducer that is cyclically stressed in bending so as to generate within its constituent material electrical charges that are collected at the surface of the component to be used by the self-powering system of the leadless capsule. The piezoelectric transducer is most often in the form of a beam clamped at one of its ends and coupled to the inertial mass at its other end, which is free.

The transducer output electrical signal is sent to a power management circuit of the capsule, which rectifies and regulates the electrical signal to output a stabilized direct voltage or current, usable to power the various electronic circuits and sensors of the capsule, and to charge the energy storage element.

Such a PEH energy harvesting device is described in particular in U.S. Pat. No. 3,456,134 A (Ko) and in above-mentioned WO 2019/001829 A1.

It will be noted that the term "beam" has to be understood in its broadest sense, i.e. an elongated, thin and flat strip, it being understood that the shape of this strip is not necessarily rectangular nor its thickness constant (as in the description of the particular embodiment that will be given hereinafter). Within the meaning of the present invention, the term "beam" hence covers elements that may have a non-constant width and/or thickness in the longitudinal direction, as well as, possibly, a deformability liable to exceed a unique degree of freedom in bending.

The problem of the invention lies in the search for simplifying the architecture of a PEH and, correlatively, the architecture of an implantable medical device self-powered by such a PEH.

Generally, with a focus on high miniaturization and integration of a PEH, it is desirable to reduce the volume occupied not only by the pendular unit itself but also by all the annex components and circuits, in such a way as to free up enough space for the oscillating beam oscillation inside the implantable device.

In this same perspective, it would also be desirable that a same structure element of the PEH can ensure several functions, in order to reduce the overall volume of the system, improve the performance, facilitate industrialization and reduce manufacturing costs.

Therefore, EP 3 876 386 A1 (Doliam), corresponding to US 2021 273587 A1 (Nguyen-Dinh et al.), proposes to make the PEH oscillating beam to fulfill, in addition to electric charge generation function, a mechanical support function for the Power Management Unit (hereafter, PMU) as well as for the PEH buffer battery. More precisely, this document proposes to laminate an interlayer insulating coating on one of the external faces of the piezoelectric layer of the PZT oscillating beam, and to add the PMU chip as well as the battery to this external interlayer. These components are fastened to the interlayer by means of a glue dot or an adhesive film, and their contact terminals are then electrically connected by a braze or a conductive glue to connecting tracks at the interlayer surface.

This arrangement allows increasing the whole system compactness and saving surface area on the printed circuit board(s) (PCBs) receiving the other electrical and electronic components of the implant.

However, from the industrialization point of view, taking into account the particular nature of the beam on which the PMU chip and the battery have to be placed, this technique is more delicate to implement than a positioning on a conventional PCB, whose material and physical characteristics (in particular, rigidity and robustness) are specifically designed to receive electronic components.

Another problem is that of optimization of the purely mechanical characteristics of the oscillating beam of the pendular unit, to modulate the bending stiffness of the PZT beam in such a way that it has a non-uniform gradient in the longitudinal direction of the beam (that is to say in the direction from the free distal end to the clamped proximal end of the beam). With a stiffness gradient, the bending stress applied to the whole structure is higher near the clamping zone, with a maximum of 50 N/mm$^2$, and tends to 0 N/mm$^2$ on the opposite side, near the inertial mass. This stress decrease is progressive and non linear due to the integration of components non-homogeneously distributed in the silicon structure.

For example, WO 2017/195014 A1 (Vermon), corresponding to US 2017/0257040 A1 (Nguyen-Dinh et al.), proposes to build the PZT beam with a composite central core (or "shim") including "posts" or "walls" whose diameters or thicknesses vary progressively between the beam distal end and proximal end. These controlled heterogeneities of the central core structure have for effect to vary correlatively the beam stiffness in the longitudinal direction, for example by making it i) more flexible in a central and/or distal region, where the deformations are the greatest—which makes it possible to increase the quantity of electric charges collected —, and ii) stiffer in a proximal region, in the vicinity of the clamp—which makes it possible to increase the mechanical robustness where the traction/compression stresses are the stronger.

This technique is however, here again, difficult and expensive to implement from the industrial point of view taking into account the extremely reduced sizes of a PZT beam when this latter is intended to power a device that needs to be extremely miniaturized, in particular when the matter is to combine in a single element (the central core) materials having different mechanical properties, to form therein the posts or the walls.

SUMMARY OF THE INVENTION

To solve the different problems and achieve the above-mentioned objects, the invention proposes a piezoelectric-transducer energy harvester, PEH, comprising a pendular unit subjected to external stresses applied to the harvester. The pendular unit comprises a beam that is elastically deformable in bending, a beam mount clamping a proximal end of the beam, and an inertial mass mounted at a free, distal end of the beam. The beam is a piezoelectric beam adapted to convert into an oscillating electric signal a mechanical energy produced by oscillations of the pendular unit. The beam comprises a flexible structure including a central core, a piezoelectric layer on at least one face of the central core, and at least one surface electrode on an external face of the piezoelectric layer.

Characteristically, according to a first aspect of the invention, the material of the central core of the flexible structure is a semiconductor material adapted to form an integrated circuit substrate, and the flexible includes at least part of components of an electric or electronic unit, said components being monolithically integrated within the semiconductor material substrate.

According to various advantageous embodiments:
an internal face, oriented towards the central core, of said piezoelectric layer is covered with an insulating interlayer, such as a parylene layer, in particular an interlayer supporting a conductive surface layer for implementing electrical connections with opposing areas of the facing central core;
the electric or electronic unit comprises components of a power management unit, PMU, integrated into the central core, the PMU being adapted to rectify and regulate the oscillating electric signal to output a stabilized direct voltage or current;
the electric or electronic unit comprises solid-state components of an energy storage element integrated in the central core, the energy storage element being adapted to be charged by the oscillating electric signal produced by the pendular unit oscillations;
the electric or electronic unit comprises components of a digital processor integrated in the central core;
the central core further includes, near the proximal end in a region non covered by a piezoelectric layer, connection pads electrically connected to components of the digital processor integrated in the central core; and/or
at least part of the components of the electric or electronic unit is integrated in a monolithic form in a distal region of the central core near, or at, the inertial mass.

The invention also encompasses a method of manufacturing a piezoelectric-transducer energy harvester, PEH, comprising forming a flexible structure including the following successive steps:

a) obtaining a central core made of a semiconductor material, adapted to form an integrated circuit substrate;

b) monolithically integrating in the flexible structure at least part of the components of an electric or electronic unit in the semiconductor material of the substrate;

c) depositing a piezoelectric layer on at least one face of the central core; and d) depositing at least one surface electrode on an external face of the piezoelectric layer.

According to various advantageous modes of implementation:

step b) comprises monolithically integrating components of a group comprising: electronic components of a power management unit, PMU, integrated to the flexible structure central core; solid-state components of an energy storage element integrated to the flexible structure central core; electronic components of a digital processor integrated to the flexible structure central core; and combinations of the preceding ones;

the method further comprises subsequent steps of: e) mounting an inertial mass at a free, distal end of the beam; and f) clamping a proximal end of the beam in a beam mount;

in particular, step e) comprises gluing half-masses directly on the respective external faces of the piezoelectric layer, and/or step f) comprises gluing two mount elements directly on the respective external faces of the piezoelectric layer.

According to a second aspect of the invention, the central core of the flexible structure is made of a semiconductor material adapted to form an integrated circuit substrate, the substrate made of a semiconductor material of the flexible structure central core includes monolithic integrated structures, and the arrangement, over the extend of the central core substrate, of said monolithic integrated structures forms in the longitudinal direction a plurality of successive areas having different piezoelectric beam bending stiffness coefficients from an area to another.

According to various advantageous embodiments:

said monolithic integrated structures are integrated electric or electronic components;

said integrated electric or electronic components are electronic components of a power management unit, PMU, integrated to the flexible structure central core, and/or solid-state components of an energy storage element integrated to the flexible structure central core, and/or electronic components of a digital processor integrated to the flexible structure central core;

the plurality of successive areas comprises, in longitudinal direction, at least one central area and adjoining distal and proximal areas, and wherein the bending stiffness of the central area is lower than the bending stiffness of the adjoining distal and proximal areas;

in particular, the distal area is at least partly located in a region of the inertial mass, and/or the proximal area is at least partially located in a region of the beam mount.

The invention also encompasses a method for manufacturing such a PEH, comprising the following steps:

a) obtaining a central core made of a semiconductor material, adapted to form an integrated circuit substrate;

b) integrating monolithic structures in the semiconductor material substrate of the central core, wherein the arrangement, over the extend of the central core substrate, of said monolithic integrated structures forms in the longitudinal direction a plurality of successive areas having different piezoelectric beam bending stiffness coefficients from an area to another;

c) depositing a piezoelectric layer on at least one face of the central core; and d) depositing at least one surface electrode on an external face of the piezoelectric layer.

According to various advantageous modes of implementation:

step b) comprises the integration in monolithic form of electric or electronic components;

said electric or electronic components integrated at step b) are electronic components of a power management unit, PMU, integrated to the flexible structure central core, and/or solid-state components of an energy storage element integrated to the flexible structure central core, and/or electronic components of a digital processor integrated to the flexible structure central core;

the method further comprises subsequent steps of: e) mounting an inertial mass at a free, distal end of the beam; and f) clamping a proximal end of the beam in a beam mount;

in particular, step e) comprises gluing half-masses directly on the respective external faces of the piezoelectric layer, and/or step f) comprises gluing two mount elements directly on the respective external faces of the piezoelectric layer.

The invention also encompasses an autonomous device housing, within a device body, an electronic unit, an energy storage element, and a PEH as described hereinabove, for powering the electronic unit and/or charging the energy storage element.

In particular, the autonomous device can be an active medical device of the implantable autonomous capsule type comprising a capsule body with an element for its anchoring to a wall of a patient's organ, the external stresses to which is subjected the pendular unit of the energy harvesting module being stresses applied to the capsule body under the effect of movements of said wall and/or blood flow rate variations in the surrounding environment.

BRIEF DESCRIPTION OF THE DRAWINGS

An exemplary embodiment of the present invention will now be described with reference to the appended drawings, in which the same references denote identical or functionally similar elements throughout the figures.

DETAILED DESCRIPTION OF PREFERENTIAL EMBODIMENTS OF THE INVENTION

An exemplary embodiment of the device of the invention will now be described, in an application to an autonomous implantable capsule intended to be implanted into a heart cavity.

As indicated hereinabove, this particular application is given only as an example of embodiment and does not limit the invention, whose teachings can be applied to many other types of autonomous devices incorporating an energy harvester of the PEH type, whether these devices are implantable or not, medical or not.

Figure 1:
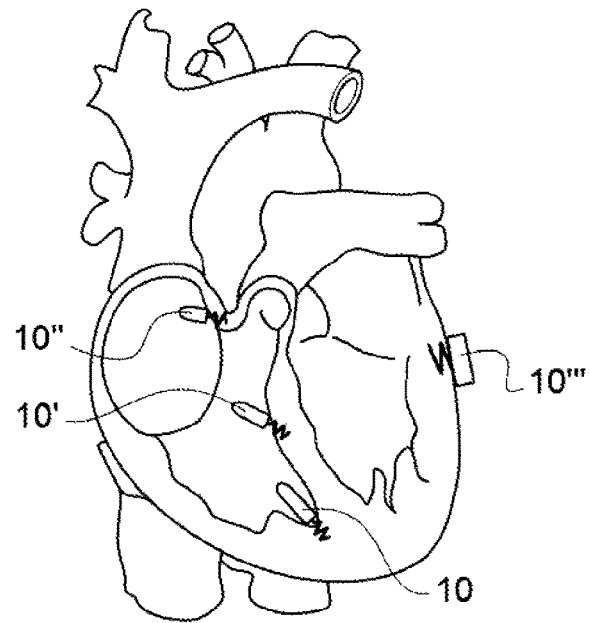
FIG. 1 illustrates medical devices of the leadless capsule type in their environment, with various examples of implantation sites in, on or near a patient's heart.

FIG. 1 shows various possibilities of implantation sites for a leadless type device in an application to cardiac pacing. Therefore, the capsule 10 is implanted inside a cavity of the myocardium (endocavitary implant), for example at the apex of the right ventricle. As an alternative, the capsule may also be implanted on the right interventricular septum, as in 10', or also on an atrial wall, as illustrated in 10". The device may also be an epicardial capsule placed on an external region of the myocardium, as illustrated in 10'''.

In any case, the leadless capsule is attached to the heart wall by means of a protruding anchoring system intended to enter the heart tissue for the holding on the implantation site. Other anchoring systems can be used, and do not change in any way the implementation of the present invention. Capsule 10 has the external form of an implant with an elongated tubular body 12 enclosing the various electronic and power supply circuits of the capsule, as well as an energy harvester with a pendular unit. The typical size of the known capsules is about 6 mm diameter for about 25 to 40 mm length.

Tubular body 12 has, at its front (distal) end 14, a protruding anchoring element, for example a helical screw 16, to hold the capsule on the implantation site. Other anchoring systems can be used, and do not change in any way the implementation of the present invention. The opposite (proximal) end 18 of capsule 10 is a free end, which is only provided with means (not shown) for the temporary connection to a guide-catheter or another implantation accessory used for implantation or explanation of the capsule, which is then detached from the latter.

Figure 2:
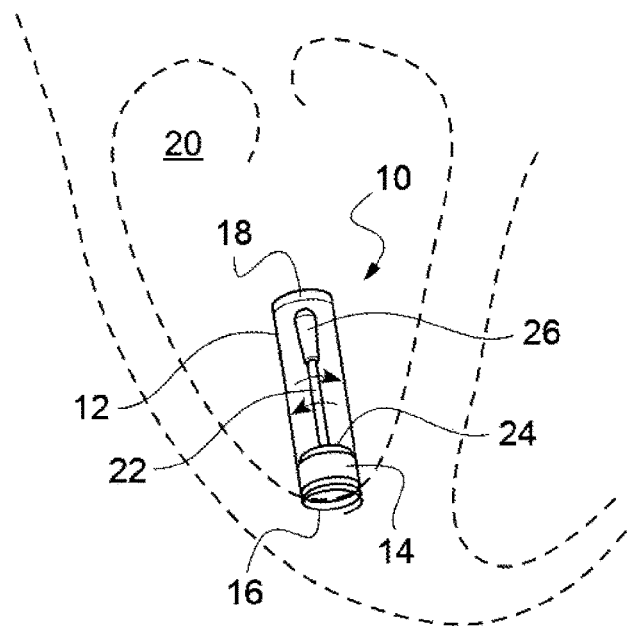
FIG. 2 illustrates a leadless capsule implanted in the bottom of the right ventricle of a patient.

In the example illustrated in FIG. 2, leadless capsule 10 is an endocavitary implant implanted into a cavity 20 of the myocardium, for example at the apex of the right ventricle. As an alternative, still in an application to cardiac pacing, the capsule can also be implanted on the interventricular septum or on an atrial wall, or also be an epicardial capsule placed on an external region of the myocardium, these different implantation modes not changing in any way the implementation of the present invention. To perform the detection/pacing functions, an electrode (not shown) in contact with the heart tissue at the implantation site collects the heart depolarization potentials and/or applies pacing pulses. In certain embodiments, the function of this electrode can be provided by anchoring screw 16, which is then an active screw, electrically conductive and connected to the detection/pacing circuit of the capsule.

Leadless capsule 10 is moreover provided with an energy harvesting module, called "PEH", comprising an inertial pendular unit that oscillates, inside the capsule, following the various external stresses to which the capsule is subjected. These stresses may result in particular from: movements of the wall to which the capsule is anchored, which are transmitted to tubular body 12 by anchoring screw 16; and/or blood flow rate variations in the environment surrounding the capsule, which produce oscillations of tubular body 12 at the rhythm of the heartbeats; and/or various vibrations transmitted by the heart tissues.

Figure 3:
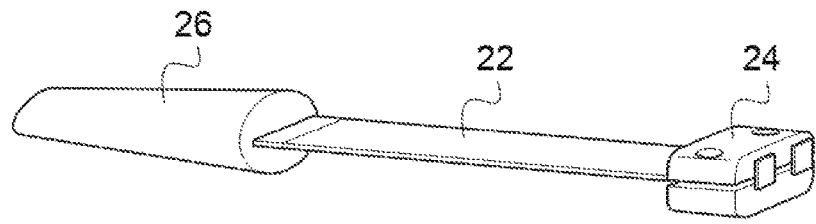
FIG. 3 shows as such a pendular unit of a known type, with a piezoelectric transducer in the form of an elongated beam clamped at one end and supporting an inertial mass at its opposite end.

The pendular unit, illustrated as such in FIG. 3, is consisted by a piezoelectric beam 22 clamped at one of its ends, at position 24, and whose opposite, free end is coupled to a mobile inertial mass 26. Piezoelectric beam 22 is an elastically deformable flexible beam that constitutes, with inertial mass 26, a pendular system of the mass-spring type. Due to its inertia, mass 26 subjects beam 22 to a deformation of the vibratory type on either side of a neutral or non-deformed position corresponding to a stable rest position in the absence of any stress. The typical minimum size of the piezoelectric transducer beams of the known devices of this type is of the order of 25 mm long for about 5 mm width. Actually, as for its mechanical behavior, this unit may be equated to a "clamped/free beam" structure, having a natural oscillation frequency, which is herein the frequency at which the mass-spring system oscillates. It will be noted that this natural oscillation frequency, typically of the order of a few tens of hertz, is noticeably higher than the frequency of the external cyclic stresses that correspond to the heartbeat frequency (at most a few hertz). Hence, at each heart contraction, the inertial mass (or other functionally similar mechanical component) will be stressed with a higher or lower amplitude, then the pendular system will oscillate several times with decreasing amplitudes (bounces characteristic of a damped periodic oscillation), and will finally stabilize up to the following heartbeat, where the stress/oscillation cycle will be comparably repeated.

Beam 22 further performs, by piezoelectric effect, a mechanical-electrical transducer function for converting into electrical charges the mechanical bending stress that is applied to it. These charges are collected by electrodes at the surface of the beam to produce an electrical signal that, after rectification, stabilization and filtering, will power the electronic circuits of the capsule.

Figure 4:
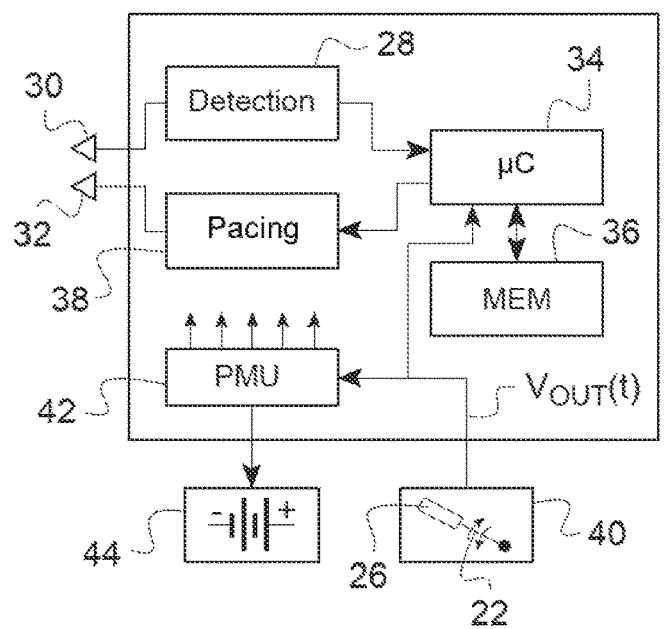
FIG. 4 schematically shows the main functional blocks of a leadless capsule.

FIG. 4 is a synoptic view of the various electric and electronic circuits integrated to the leadless capsule, presented as functional blocks.

Block 28 denotes a heart depolarization wave detection circuit, which is connected to a cathode electrode 30 in contact with the heart tissue and to an associated anode electrode 32, for example a ring electrode formed on the tubular body of the capsule. Detection block 28 comprises filters and means for analog and/or digital processing of the collected signal. The so-processed signal is applied to the input of a microcomputer 34 associated with a memory 36. The electronic unit also includes a pacing circuit 38 operating under the control of microcomputer 34 to provide to the system of electrodes 30, 32 myocardial pacing pulses.

An energy harvesting circuit or PEH 40 is moreover provided, consisted by the pendular unit formed by piezoelectric beam 22 and inertial mass 26, described hereinabove with reference to FIGS. 2 and 3. As piezoelectric beam 22 also ensures a mechanical-electrical transducer function, it converts into electrical charges the mechanical stresses undergone and produces a variable electrical signal $V_{OUT}(t)$, which is an alternating signal oscillating at the natural oscillation frequency of the pendular beam 22/mass 26 unit, and at the rhythm of the successive beats of the myocardium to which the capsule is coupled.

The variable electrical signal $V_{OUT}(t)$ is sent to a power management circuit or PMU 42. PMU 42 rectifies and regulates the signal $V_{OUT}(t)$ so as to output a stabilized direct voltage or current for powering the various electronic circuits and charging the integrated battery 44.

On the other hand, the beam is advantageously a beam of the bimorphous type, i.e. capable of generating energy on its two faces when subjected to a deformation. Theses transduction properties are typical of a piezoelectric material, such as PZT (lead titanium-zirconate) ceramics or PMN-PT (barium titanate or lithium niobate) mono-crystals.

Figure 5:
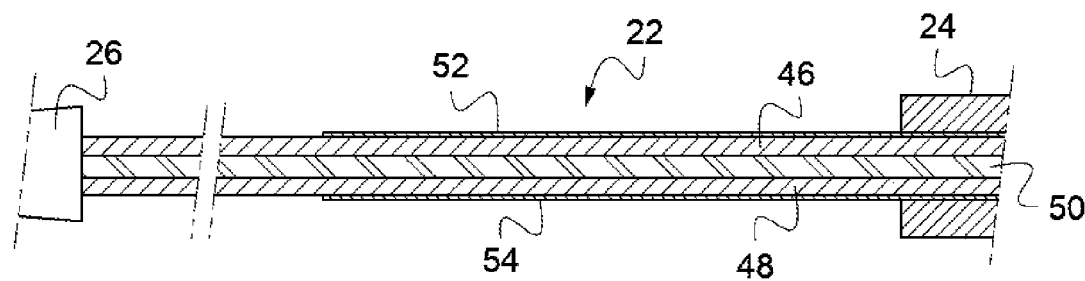
FIG. 5 is a cross-sectional view showing, with a deliberately exaggerated thickness scale, the structure of the different layers of a bimorphous piezoelectric transducer usable with the present invention.

FIG. 5 schematically illustrates, with a deliberately exaggerated thickness scale, the structure of the different layers of such a bimorphous piezoelectric beam.

Bimorphous beam 22 comprises two layers 46, 48 of piezoelectric ceramic material, for example a PZT ceramic, deposited on each of the opposite faces of a central core or "shim" 50.

Central core 50 is generally made of a conductive material such as brass, but it has also been proposed to make it of an insulating material, with in this case contact bridges for shunting the internal electrodes of the piezoelectric layers.

The bimorphous structure illustrated corresponds in fact to the association of two unimorphous structures placed back-to-back with, in common, the central core supporting the piezoelectric material (this material being supported on only one face of the central core in the case of a unimorphous structure and on both faces in the case of a bimorphous structure).

Actually, all that will be explained in the following examples, that show a bimorphous structure, is transposable as well to a unimorphous structure, with the same transducer component and element arrangements, but on only one side of the central core instead of both sides, the teachings of the invention applying in the same manner.

In a conventional structure such as that of FIG. 5, in which core 50 is made of a conductive material, typically brass, the charges produced by deformation of the piezoelectric layers 46, 48 material are collected, on the external side, by surface electrodes 52, 54 deposited on opposite faces of the beam, and on the internal side, by the conductive central core 50.

In a simplified version illustrated here, the beam geometry is rectangular in shape, with a typical maximum width of 5 mm and a maximum length of 35 mm. The thickness of the piezoelectric layers 46, 48 arranged on either side of the silicon central core is typically of 300 µm.

As described in EP 3 930 014 A1 (Cairdac), in order to reinforce the reliability of beams 22, 22', it is possible to give these latter, over all or part of their length, a trapezoidal shape in plan view, with a (linear or exponential) width decrease for a better distribution of the stresses along the beam, these stresses being stronger near and at clamp 24, and null at inertial mass 26. Moreover, the trapezoidal shape makes it possible to adjust the resonant frequency of the unit as a function of the trapezoidal geometry, while maximizing the amplitude of displacement of the mass due to the fact that the free end is narrower than the clamped end.

Figure 6:
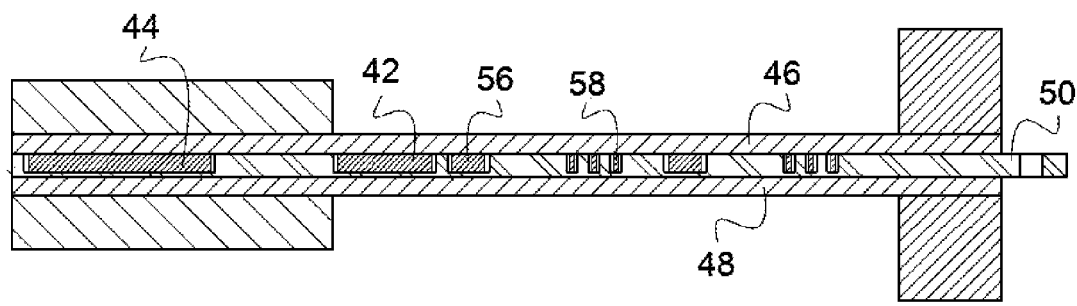
FIG. 6 is a cross-sectional view showing, with a deliberately exaggerated thickness scale, the structure of the different layers of a bimorphous piezoelectric transducer according to the invention, in a first embodiment in which the piezoelectric beam central core integrates monolithic electronic components.

FIG. 6 is similar to FIG. 5, for a piezoelectric transducer arranged according to a particular embodiment of the invention, with integration of monolithic components.

As mentioned hereinabove, in known piezoelectric transducers, the central core is generally made of a metallic material such as brass, in particular to allow a direct connection with the overlying piezoelectric layer, and thus the capture of the charges produced by the piezoelectric material deformation.

According to the invention, this central core is not made of a metallic material, nor an insulating material, but of a semiconductor material, and this semiconductor central core forms in particular a substrate in which monolithic structures can be integrated.

These monolithic structures can advantageously (but not necessarily) comprise integrated electric or electronic components.

These electric or electronic components can advantageously (but not necessarily) comprise the energy management circuit PMU 42 and/or the integrated battery 44, the roles of which have been described hereinabove with reference to FIG. 4.

Other components, whether electronic or electric, active or passive, denoted 56, 58, . . . , can also be integrated to the substrate of core 50 in a monolithic form.

Those various monolithic structures can be made by means of conventional microchip manufacturing techniques: etching, epitaxy, masking, layer deposition, etc., per se well known and that won't be described in detail.

The semiconductor material is advantageously silicon, taking into account its good mechanical properties and the possibility to make therein various integrated monolithic structures by easy-to-implement techniques, and all this on a very small thickness, typically at most 10 to 20 µm. It is indeed necessary that the central core 50, and hence the piezoelectric transducer beam, keeps sufficient flexibility so that the piezoelectric transducer layers can be deformed and produce the electrical charges as desired.

For the sake of convenience, a silicon central core will be considered hereinafter, but the choice of this material is in no way limiting of the invention and other semiconductor materials can be used as well to implement the teachings of the invention, as will become clear from the following description of the different embodiments exposed hereinafter.

According to a first aspect of the invention, the monolithic integrated structures of the beam central core are components of integrated electric or electronic units associated with the PEH and/or to the device powered by this PEH (seen differently, according to the invention, the substrate of a microchip of the PEH supports a piezoelectric material layer on at least one of its faces).

In a first, particularly advantageous implementation, the monolithic integrated structures are components of a PMU directly coupled to the charge collection electrodes of the piezoelectric beam, i.e. a PMU such as that denoted 42 in FIG. 4, which receives and processes the charges produced by the piezoelectric material deformation.

The management of the energy produced by the piezoelectric beam and the output of a regular power supply voltage or current by the PMU can therefore be at least partially, and preferably totally, integrated to the pendular unit i) without the need of any additional component on the beam (as in above-mentioned WO 2017/195014 A1, in which the PMU chip is an added component, supported by the beam), and ii) without connection of the beam electrodes to a remote circuit located on a PCB arranged in the device near the PEH but separately from the latter (as in the conventional configuration of above-mentioned WO 2019/001829 A1).

Therefore, the PEH according to the invention is in the simple form of a pendular unit (piezoelectric beam+inertial mass+beam mount) with output pads providing regulated voltage or current directly usable for powering a device associated with this PEH. The device then requires no proper PMU nor regulation circuit specifically adapted to the PEH used. In a second implementation, as an alternative or—advantageously—a complement of the preceding one, some monolithic integrated structures are components of a solid-state battery powered with the charges generated by the piezoelectric beam oscillations. Solid-state batteries are components per se well known, in particular solid-state lithium batteries that can advantageously replace lithium-ion or lithium-polymer liquid batteries. Solid-state batteries are made by deposition of thin lithium layers on a silicon substrate, with methods per se known which won't be described in more detail.

In a third implementation, as an alternative or a complement of the previous ones, the monolithic integrated structures are components of the device powered by the PEH according to the invention, in particular:

components of a digital processor (such as microcontroller 34 of FIG. 4), and/or components of a stimulation or detection circuit (circuits 28 and 38 in FIG. 4), and/or active components (in particular, diodes) or passive components (resistors, capacitors, etc.).

In any case, the integration of monolithic electric or electronic components in the central core of the PZT beam helps in increasing whole compactness of the device and in simplifying the industrial making of the latter.

According to a second aspect of the invention, the monolithic integrated structures serve to apply to the beam a bending stiffness gradient differentiated in longitudinal direction (that is to say between the free distal end and the clamped proximal end).

More precisely, the differentiated arrangement of the monolithic integrated structures formed in the silicon substrate of the central core makes it possible to define a plurality of successive areas having beam bending stiffness coefficients that are different from an area to another.

Figure 7:
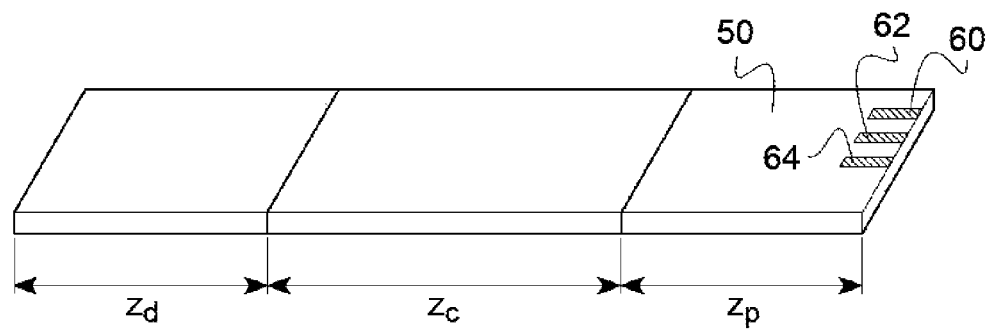
FIG. 7 provides a general illustration of how to obtain in the longitudinal direction a variable stiffness gradient over the extent of the piezoelectric beam, according to the teachings of the invention.

Therefore, as illustrated in FIG. 7 that shows as such the piezoelectric beam in perspective, it is possible to design:

a more flexible central area $z_c$, where the bending stresses are more important, in such a way as to favor the production of electric charges in the piezoelectric material in this area; and/or a more rigid distal end area $z_d$ or proximal end area $z_p$, where the bending stresses are lesser, but where it is desirable to increase the mechanical stiffness of the beam to support the inertial mass (distal side) and to ensure a robust clamping of the beam into its mount (proximal side).

The monolithic integrated structures arranged in central core 50 to define the differentiated bending stiffness gradient according to the areas may be electric or electronic components such as those exposed hereinabove about the first embodiment.

But this is only a possibility, and all or part of the monolithic integrated structures defining the stiffness gradient can be non-electrically functional structures, having themselves only a mechanical role.

The lengths of each of the three areas $z_d$, $z_c$ and $z_p$ are typically lower than 15 mm, with a width typically lower than 5 mm, these values being of course given here by way of illustration.

It should be noted that the integration of battery 44 into a distal region of central core 50 near, or at, inertial mass 26 makes it possible to locally increase the mass of the inertial mass 26 by the proper mass of battery 44, thus favoring the oscillation behavior of the pendular unit.

FIGS. 8 to 11 illustrate in more detail the internal structure of a PEH made according to the first aspect of the invention indicated hereinabove, namely with monolithic integration of elements having an electric or electronic functionality.

Figure 8:
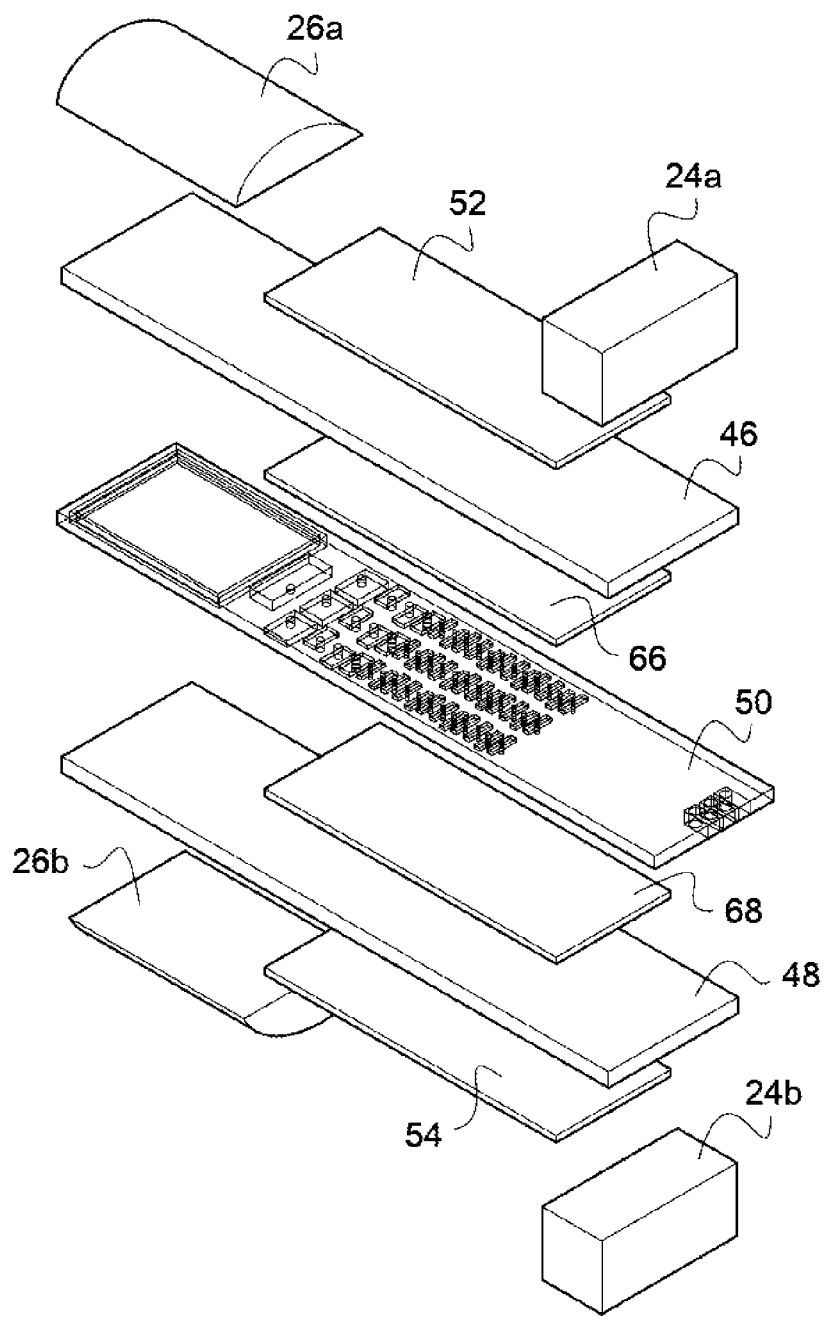
FIG. 8 is an exploded view of a piezoelectric transducer according to the invention as that of FIG. 6 in an embodiment integrating monolithic components, this view showing separately the different constituent parts of the transducer.
Figure 9:
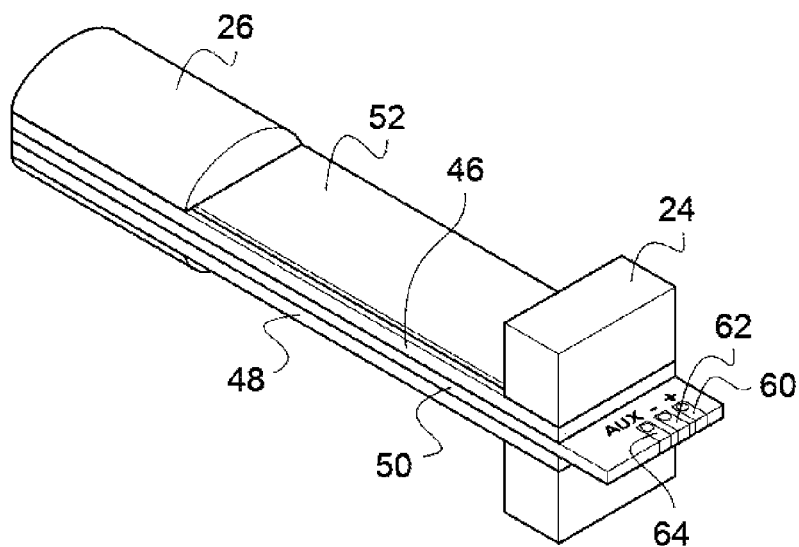
FIG. 9 is a perspective view of the piezoelectric transducer of FIG. 8, in a final assembled configuration.

As can be seen in the exploded view of FIG. 8 and in the final configuration view of FIG. 9, the PEH according to the invention comprises central core 50 with, on either side, a piezoelectric material layer 46, 48 (in the case of a PEH beam of the bimorphous type; in the case of a unimorphous beam, the piezoelectric layer would be present only on one of the faces of central core 50).

On their external face, the piezoelectric layers 46, 48 include a respective conductive electrode 52, 54 for collecting the electric charges.

On their internal face, i.e. the face towards central core 50, the piezoelectric layers 46, 48 are covered with an insulating interlayer, respectively 66, 68, made for example by deposition of parylene. Parylene is a polymer that can be vacuum deposited and receive a conductive surface layer for the making of various electrical connections between predefined points of the layer, corresponding to areas facing central core 50 and requiring a contact, selectively on each of the electric or electronic elements integrated to central core 50.

Figure 10:
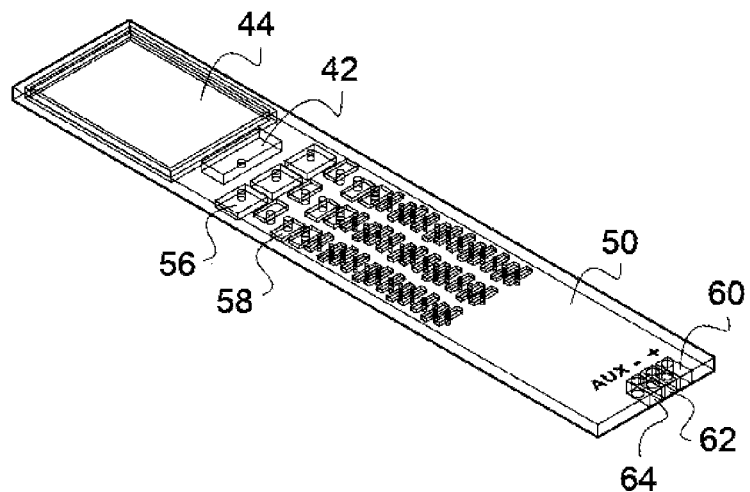
FIG. 10 shows as such, in a perspective view, the central core of the piezoelectric beam of the transducer of FIG. 8.

As can be seen in FIG. 10 that shows central core 50 as such, the latter integrates a number of electric or electronic elements such as: solid-state battery 44, PMU 42, various digital or analog circuit chips 56, active or passive components 58, etc. The interconnections between these various elements, and with the internal electrodes formed on the intermediate layers 66, 68, are performed by means of vias, or directly against a conductive layer of the interlayer 66, 68.

Figure 11:
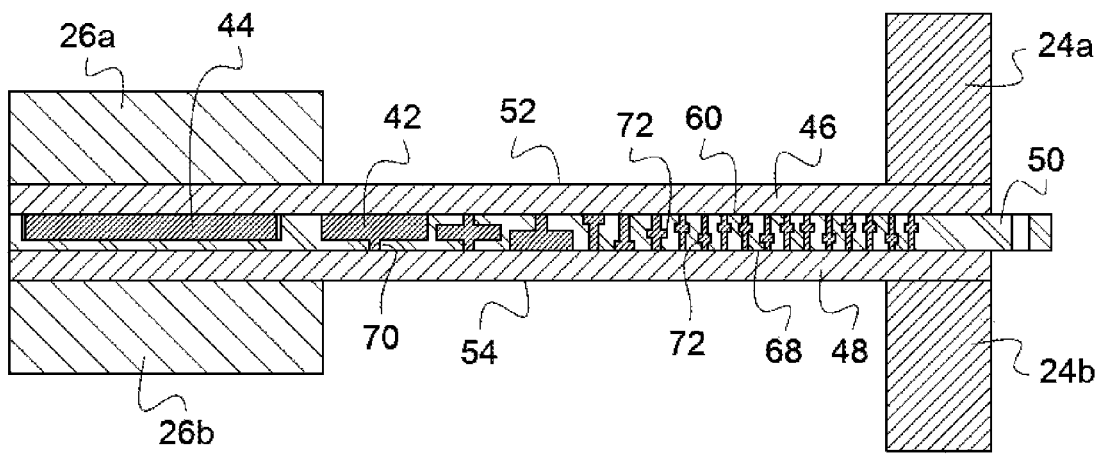
FIG. 11 is an enlarged detail, in cross-sectional view, of the piezoelectric transducer beam of FIGS. 8 to 10, this view showing the way to realize the interconnections within the different layers of the central core, and between these layers and the internal surfaces of the piezoelectric layers of the beam.

For example, as can be seen in the cross-sectional view of FIG. 11, PMU 42 is in direct electrical connection with a conductive area of the internal surface of layer 46, just like one of the terminals of battery 44, whereas another terminal of this same PMU is connected to a specific contact point through a via, as that illustrated in 70. Other vias, as those illustrated in 72, provide interconnections between the various layers of the semiconductor substrate of central core 50, as well as possibly with conductive areas of the internal face of the intermediate layers 46, 48.

In an embodiment in which the internal core integrates all the components required for the powering circuit of an electronic device, the proximal end can be ended by connection pads 60, 62, 64, for example a positive pad (+) 60, a negative pad (−) 62 and an auxiliary pad (AUX) 64, the electronic device powered by the PEH of the invention being simply connected to these terminals as it would be to a simple cell or battery.

In this configuration, the PEH incorporates, characteristically of the invention, the totality of the elements for energy collection, intermediate storage (by battery 44) and regulation (by PMU 42).

The auxiliary path may serve in particular for an external charging of the battery when the device is in a condition of prolonged storage before implantation, as described for example in EP 4 019 083 A1, EP 4 015 034 A1 and EP 4 015 036 A1 (Cairdac).

Figure 12:
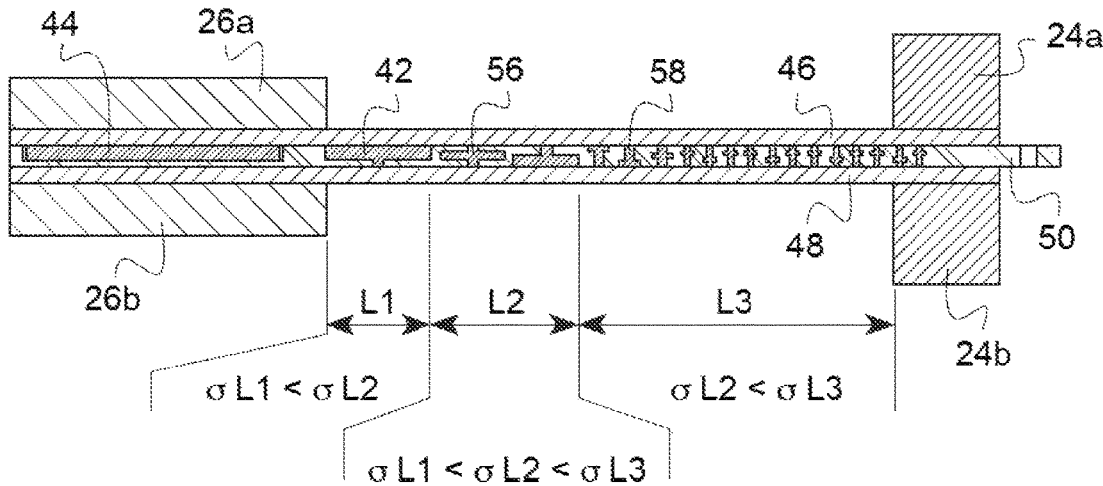
FIG. 12 illustrates the way the variable stiffness gradient is distributed over the extent of the piezoelectric beam of the embodiment of FIG. 11.
Figure 13:
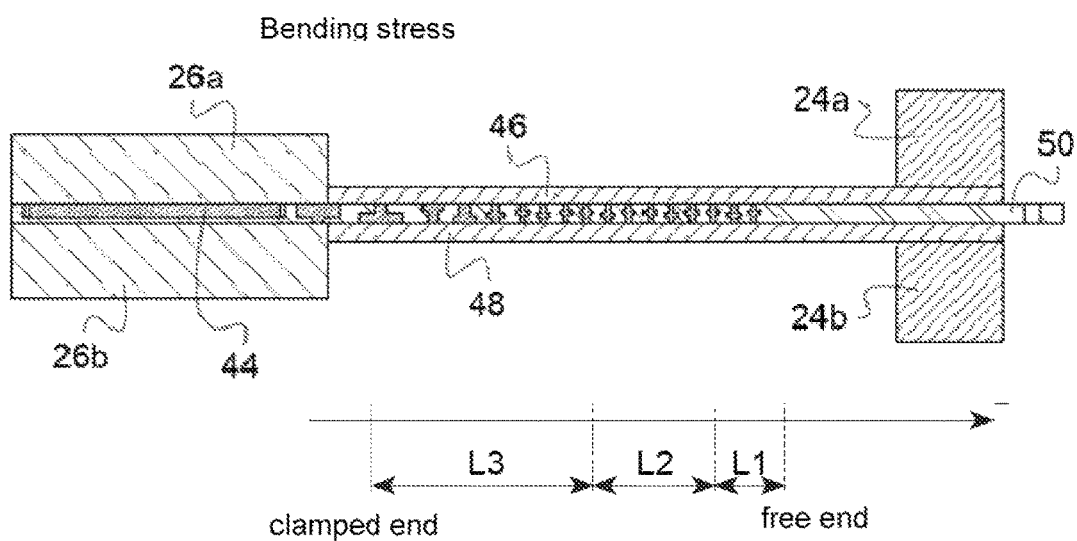
FIG. 13 is a curve showing the stiffness gradient variation characteristic as a function of the distance for the piezoelectric beam illustrated in FIG. 12.

FIG. 12 illustrates the way the variable stiffness gradient is distributed over the extent of the piezoelectric beam of the embodiment of FIG. 11, and FIG. 13 is a curve showing the stiffness gradient variation characteristic as a function of the distance for this piezoelectric beam.

On the unit formed by the silicon central core 50, PZT layers 46, 48 and surface electrodes 52, 54, the bending stress—exerted decreases on a regular basis with the distance (successive areas L3, L2 and L1) from the clamping point of the mount 24. In the embodiment illustrated, the typical bending stress does not exceed a critical value of 50 N/mm$^2$.

Therefore, the integration of non-homogeneously distributed components in the structure of the silicon central core 50 introduces such a stiffness gradient that the bending stress applied to the whole structure decreases in a progressive and non-linear manner; this stress is higher near the clamping area, with a maximum admissible of 50 N/mm$^2$, and tends to 0 N/mm$^2$ on the opposite side, near the inertial masses.

Figure 14:
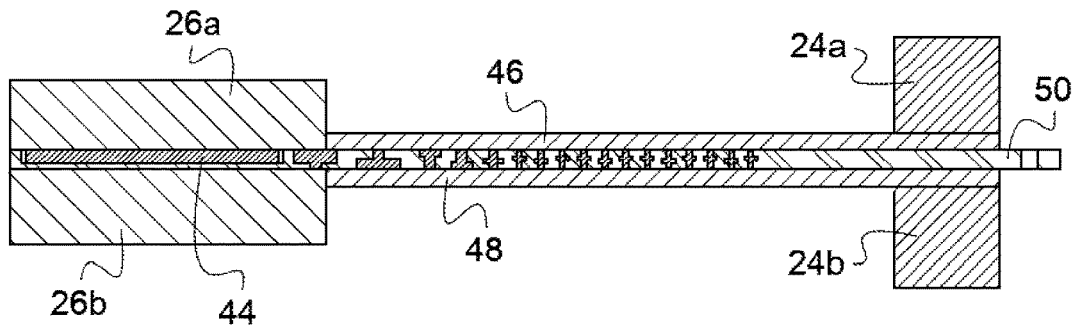
FIG. 14 is similar to FIG. 11, for an alternative embodiment of the transducer.

FIG. 14 is similar to FIG. 11, for an alternative embodiment of the transducer.

In this alternative, instead of extending up to the distal end of central core 50, both PZT layers 46, 48 are shorter and are not covered by the inertial half-masses 26a, 26b. The advantage of this configuration is that it favors the space available for the mass amplitude during the sub-assembly oscillation. The available space is thus optimized in terms of embedded density and assembly deflection. The volume gain, typically about 10%, can be transferred to the inertial masses or to the sub-assembly oscillation (typically 0.5 mm), which makes it possible to increase the electrical performances of the energy harvesting system.

Figure 15:
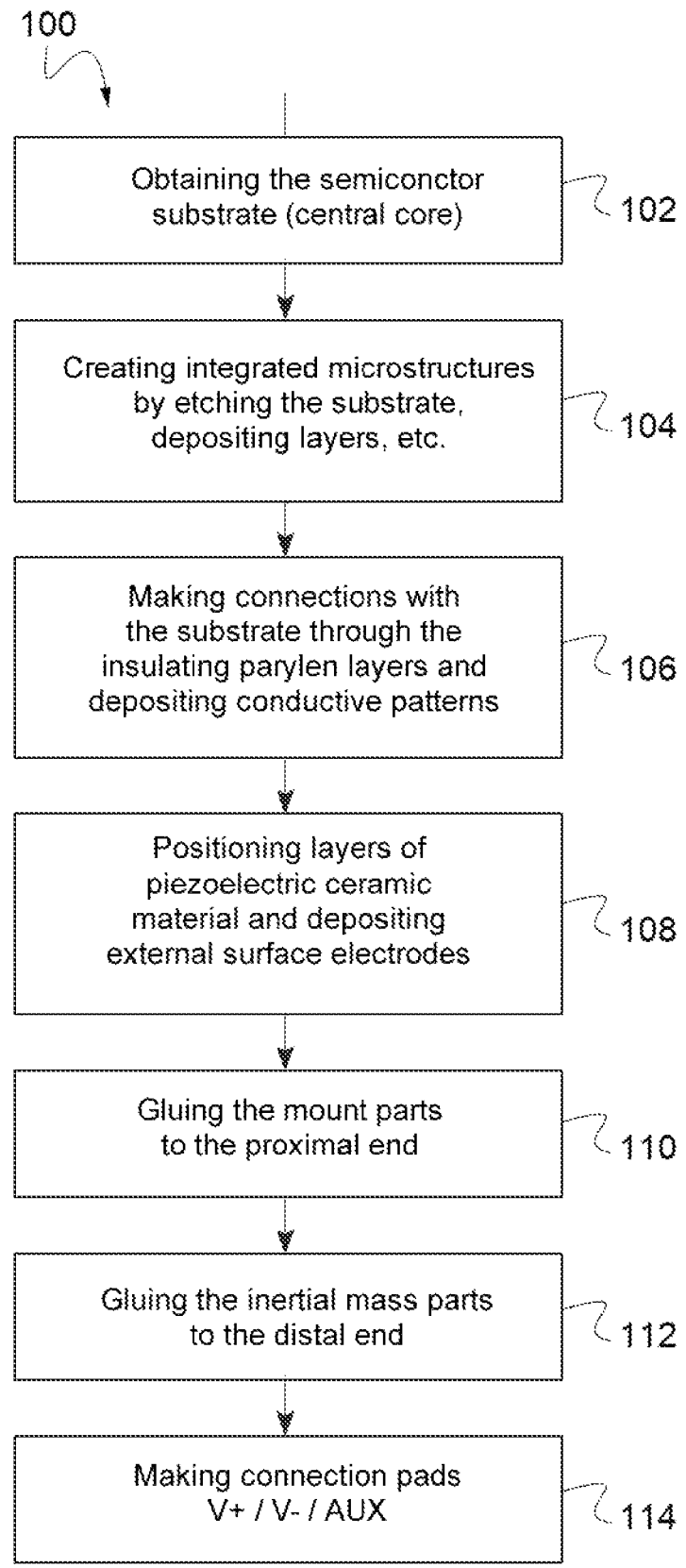
FIG. 15 is a flowchart showing the different steps of a PEH manufacturing method according to the invention.

FIG. 15 is a flowchart showing the different steps of a PEH manufacturing method according to the invention, such as that just described hereinabove.

The first step (block 102 of the flowchart 100) of FIG. 12 consists in obtaining central core 50 from a semiconductor material (typically silicon) adapted to form an integrated circuit substrate.

The following step (block 104) consists in creating the integrated microstructures by etching the semiconductor substrate, depositing conductive or insulating layers, etc., by manufacturing techniques per se well known, used without particular adaptation and that won't be described in detail.

The following step (block 106) consists in depositing the intermediate parylene intermediate layers 66, 68. These layers, whose surface will have been etched in such a way as to define electrical traces with, as a resist, non-electrically conductive areas, provide connection with the substrate and interconnections between the different microstructures.

The following step (block 108) consists in positioning on the unit formed by central core 50 and interlayers 66, 68, the piezoelectric ceramic material layers 46, 48, on which are deposited surface electrodes 52, 54 for electric charge collection.

The following step (block 110) consists in gluing to the proximal end (corresponding to the clamped end) of the so-obtained beam the elements 24a, 24b of the mount.

The following step (block 112) consists in gluing to the distal end (corresponding to the oscillating free end) of the beam the two halves 26a, 26b of the inertial mass.

The final step (block 114) consists in materializing, on the proximal side of the beam, the connection pads 60, 62, 64 enabling subsequent connection to the electric circuits of the device to be powered by the so-formed PEH. The unit is then in its final assembled state, as illustrated in FIG. 9.

The invention claimed is:

1. A piezoelectric-transducer energy harvester, PEH, comprising a pendular unit subjected to external stresses applied to the harvester, the pendular unit comprising:
    a beam that is elastically deformable in bending;
    a beam mount clamping a proximal end of the beam; and
    an inertial mass, mounted at a free, distal end of the beam,
    wherein the beam is a piezoelectric beam adapted to convert into an oscillating electric signal a mechanical energy produced by oscillations of the pendular unit,
    wherein the piezoelectric beam comprises a flexible structure including: a central core; a piezoelectric layer on at least one face of the central core; and at least one surface electrode on an external face of the piezoelectric layer,
    wherein the central core of the flexible structure is a semiconductor material adapted to form an integrated circuit substrate,
    wherein the substrate made of a semiconductor material of the flexible structure central core includes monolithic integrated structures,
    and wherein the arrangement, over the extend of the central core substrate, of said monolithic integrated structures forms in the longitudinal direction a plurality of successive areas having different piezoelectric beam bending stiffness coefficients from an area to another.

2. The PEH of claim 1, wherein said monolithic integrated structures are integrated electric or electronic components.

3. The PEH of claim 2, wherein said integrated electric or electronic components are components of a group comprising: electronic components of a power management unit, PMU, integrated to the flexible structure central core; solid-state components of an energy storage element integrated to the flexible structure central core; electronic components of a digital processor integrated to the flexible structure central core; and combinations of the preceding ones.

4. The PEH of claim 1, wherein the plurality of successive areas comprises in longitudinal direction at least one central area, and adjoining distal and proximal areas, and wherein the bending stiffness of the central area is lower than the bending stiffness of the adjoining distal and proximal areas.

5. The PEH of claim 4, wherein the distal area is at least partially located in a region of the inertial mass.

6. The PEH of claim 4, wherein the proximal area is at least partially located in a region of the beam mount.

7. An autonomous device housing, within a device body:
    an electronic unit;
    an energy storage element; and a piezoelectric-transducer energy harvester, PEH, for powering the electronic unit and/or charging the energy storage element, wherein the PEH comprises a pendular unit subjected to external stresses applied to the harvester, wherein the pendular unit comprises: a beam that is elastically deformable in bending; a beam mount clamping a proximal end of the beam; and an inertial mass mounted at a free, distal end of the beam, wherein the beam is a piezoelectric beam adapted to convert into an oscillating electric signal a mechanical energy produced by oscillations of the pendular unit, wherein the piezoelectric beam comprises a flexible structure including: a central core; a piezoelectric layer on at least one face of the central core; and at least one surface electrode on an external face of the piezoelectric layer, wherein the central core of the flexible structure is a semiconductor material adapted to form an integrated circuit substrate, wherein the substrate made of a semiconductor material of the flexible structure central core includes monolithic integrated structures, and wherein the arrangement, over the extend of the central core substrate, of said monolithic integrated structures forms in the longitudinal direction a plurality of successive areas having different piezoelectric beam bending stiffness coefficients from an area to another.

8. The autonomous device of claim 7, wherein the autonomous device is an active medical device of the implantable autonomous capsule type comprising a capsule body with an element for its anchoring to a wall of a patient's organ, and wherein the external stresses to which is subjected the PEH are stresses applied to the capsule body under the effect of movements of said wall and/or flow rate variations of a flow in a surrounding environment.

9. A method for manufacturing a piezoelectric-transducer energy harvester, PEH, comprising the following successive steps:

a) obtaining a central core made of a semiconductor material, adapted to form an integrated circuit substrate;

b) integrating monolithic structures in the semiconductor material substrate of the central core, wherein the arrangement, over the extend of the central core substrate, of said monolithic integrated structures forms in the longitudinal direction a plurality of successive areas having different piezoelectric beam bending stiffness coefficients from an area to another;

c) depositing a piezoelectric layer on at least one face of the central core; and d) depositing at least one surface electrode on an external face of the piezoelectric layer.

10. The method of claim 9, wherein step b) comprises the integration in monolithic form of electric or electronic components.

11. The method of claim 10, wherein said electric or electronic components integrated at step b) are components of a group comprising: electronic components of a power management unit, PMU, integrated to the flexible structure central core; solid-state components of an energy storage element integrated to the flexible structure central core; electronic components of a digital processor integrated to the flexible structure central core; and combinations of the preceding ones.

12. The method of claim 9, further comprising subsequent steps of:

e) mounting an inertial mass at a free, distal end of the beam; and f) clamping a proximal end of the beam in a beam mount.

13. The method of claim 12, wherein step e) comprises gluing half-masses directly on respective external faces of the piezoelectric layer.

14. The method of claim 12, wherein step f) comprises gluing two mount elements directly on respective external faces of the piezoelectric layer.

* * * * *